(12) United States Patent
Brehm et al.

(10) Patent No.: US 6,550,336 B2
(45) Date of Patent: Apr. 22, 2003

(54) PROBE FOR MEASURING PRESSURE OSCILLATIONS

(75) Inventors: Armin Brehm, Nussbaumen (CH); Wolfgang Evers, Nussbaumen (CH); Hugo Wetter, Buchs (CH); Hanspeter Zinn, Baden-Rütihof (CH)

(73) Assignee: Alstom (Switzerland) Ltd, Baden (SE)

( * ) Notice: Subject to any disclaimer, the term of this patent is extended or adjusted under 35 U.S.C. 154(b) by 0 days.

(21) Appl. No.: 09/991,966

(22) Filed: Nov. 26, 2001

(65) Prior Publication Data

US 2003/0024318 A1 Feb. 6, 2003

(30) Foreign Application Priority Data

Dec. 1, 2000 (DE) .......................... 100 59 701

(51) Int. Cl.⁷ ................................ G01L 7/00
(52) U.S. Cl. ....................................... 73/707
(58) Field of Search ................... 73/701, 702, 703, 73/707, 715, 716, 717, 718, 719, 720–727, 40.7, 49.5, 49.6, 756; 181/102, 104; 702/6; 367/25, 43

(56) References Cited

U.S. PATENT DOCUMENTS

| 4,517,842 A | * | 5/1985 | Twomey et al. ............... 73/701 |
| 4,934,375 A | * | 6/1990 | Cole et al. ..................... 600/486 |
| 5,551,439 A | * | 9/1996 | Hickey ......................... 600/486 |
| 5,831,934 A | * | 11/1998 | Gill et al. ...................... 367/25 |
| 5,936,913 A | * | 8/1999 | Gill et al. ...................... 367/25 |
| 6,053,048 A | | 4/2000 | Keller ........................... 73/707 |

FOREIGN PATENT DOCUMENTS

| DE | 34 23 178 C1 | 4/1985 |
| DE | 196 02 048 A1 | 7/1997 |
| DE | 197 35 724 A1 | 2/1999 |
| DE | 197 48 578 A1 | 5/1999 |
| DE | 693 25 586 T2 | 7/1999 |
| DE | 199 03 941 A1 | 8/2000 |
| GB | 2 037 993 A | 7/1980 |
| JP | 06-331146 A | 11/1994 |

* cited by examiner

*Primary Examiner*—William Oen
(74) *Attorney, Agent, or Firm*—Burns, Doane, Swecker & Mathis, L.L.P.

(57) ABSTRACT

A probe for measuring pressure oscillations includes an inner tube functioning as a measuring tube, an outer tube positioned so as to envelop the measuring tube, a toroidal space open to one side being defined between an outer wall of the measuring tube and an inner wall of the outer tube, a pressure transmitter, which is in connection with the interior of the measuring tube in the area of a transmitter end of the measuring tube, and a semi-infinite tube, which is connected at a first end to the transmitter end of the measuring tube, and which is connected at a second end to the toroidal space. The semi-infinite tube is constructed as a winding positioned around at least one of the measuring tube and the outer tube, thereby providing a compact and robust construction of a probe module, which is suitable especially for continuous use in the measuring of combustor pulsations in gas turbines.

12 Claims, 3 Drawing Sheets

PROBE FOR MEASURING PRESSURE OSCILLATIONS

FIELD OF THE INVENTION

The present invention relates to a probe for measuring pressure oscillations, and in particular to probes for measuring pressure oscillations in combustors of gas turbines. The invention also relates to the use of probes according to the invention.

BACKGROUND OF THE INVENTION

Pressure oscillations occurring in the combustors of modern gas turbines, so-called combustor pulsations or combustion pulsations, often also simply called pulsations, provide important indications of the quality of the combustion, especially when employing premix burner technology. Under unfavorable conditions, the combustor pulsations may reach amplitudes at which the mechanical integrity of gas turbine components is at risk. This means that a permanent monitoring of combustor pressure oscillations basically is now indispensable. Because of the high temperatures, a direct detection of occurring pressure oscillations requires high-temperature-resistant pressure sensors, which on the one hand are very expensive, and on the other hand are confronted with usage conditions that are so extreme that a significant probability of failure exists during continuous operation. It is also known that the sensor characteristic of such sensors is temperature-dependent, which also makes the quantification of the measured pressure oscillations harder or allows it only with limited accuracy. In order to not expose the sensors to excessive temperatures, they are set back from the combustor wall a distance by means of an adapter. However, such an adapter has a resonance behavior that influences the acoustic signal. Similar tasks for identical problems encountered in the realization of a measuring device naturally exist also in other combustors and hot gas flows.

For this reason, the use of so-called long-line probes is known. In these, the actual measuring point within the gas turbine combustor is connected by means of a line, basically by means of a small tube, with a pressure transmitter positioned outside of the combustor. This makes it possible that the transmitter can be used at substantially lower temperatures. For this reason, substantially cheaper pressure transmitters or microphones, whose useful life and measuring accuracy is not limited by extreme usage conditions, can be used. In such a configuration, it is important to ensure an echo-free termination of the measuring line formed in this manner, and, if possible, to also avoid any type of reflections within the measuring line.

The termination of the measuring tube with a semi-infinite tube is known. This is realized with a line having a long length. The line or semi-infinite tube is connected at a first end with the end of the measuring tube opposite from the end that faces the measuring point. With sufficient length, the pressure oscillations are attenuated inside the semi-infinite tube as a result of internal dissipation in such a way that no significant amplitude reflections remain at the second end of the semi-infinite tube. According to the state of the art, the second end of the semi-infinite tube is simply closed off in order to prevent hot gas leaks. The disadvantage of this is that the entire measuring device is filled with hot and aggressive combustion gases, and the transmitter is again exposed to elevated loads. Furthermore, conventional long-line probes with coupled semi-infinite lines are difficult to handle in practice, since the current state of the art does not offer any solution as to how to include the semi-infinite tube as an integral component of the probe. This means that the state of the art does not offer any solution, in which an easily manageable, robust, and compact probe is available for measuring pressure oscillations in combustors, in which probe the pressure transmitter is positioned at a distance from the actual, thermally loaded measuring point.

SUMMARY OF THE INVENTION

In view of the above-disadvantages with the prior art, an embodiment of the invention provides a so-called long-line probe for measuring pressure oscillations in combustors, with the long-line probe being easily manageable, compact, and robust. The probe according to the invention can be used in a frequency range from 0 Hz to 10 kHz without any significant falsification of the signals due to resonances that may occur. In the interest of better handling, the probe is preferably a compact embodiment. Any potentially necessary supply lines are integrally embodied in this probe in order to prevent a risk of damaging external connection lines as much as possible. The probe must be suitable for maintenance-free continuous operation of several tens of thousands of operating hours. Should any damage occur, a simple, quick replacement of the entire probe module must be possible.

According to a preferred embodiment of the invention, the probe includes the following elements:

- an inner tube functioning as a measuring tube, with one end of the inner measuring tube being positioned on the measuring point side of the probe, and the opposite end of the measuring tube being positioned on the transmitter side of the probe;
- an outer tube, which is positioned so as to envelop the measuring tube at least partially, and an outer wall of the measuring tube and an inner wall of the outer tube defining therebetween a toroidal space open to one side;
- a pressure transmitter, which is in connection with the interior of the inner measuring tube in the area of the transmitter-side end of the measuring tube; and
- a semi-infinite tube, which is connected at a first end to the transmitter-side end of the measuring tube, and which is connected at a second end to the toroidal space, the semi-infinite tube being constructed as a winding positioned around at least one of the measuring tube and the outer tube.

In one preferred embodiment, the inner measuring tube is provided at its outer wall with a thermal insulation. With the help of this measure, temperature gradients within the measuring tube that would influence the measuring result are avoided as much as possible.

The formation of the semi-infinite tube as a winding around an actual probe tube ensures a compact design. Furthermore, a robust connector for a flushing gas can be provided via the outer tube. This makes it possible to flush the semi-infinite tube and the measuring tube with a flushing gas, so that a penetration of combustion gases into the actual measuring technology is prevented. The flushing gas furthermore helps in preventing the occurrence of temperature gradients in the measuring tube.

In order to avoid undesired reflections, within the measuring tube, the length of the semi-infinite tube is preferably more than 7000 times its diameter. Advantageous embodiments of the invention have semi-infinite tube lengths of more than 40 meters, and even more preferably equal to or greater than 50 meters. In order to avoid interfering seams that again would result in reflections with echo effects, it is also advantageous in this connection that the semi-infinite tube has the same internal diameter as the measuring tube. These internal diameters are selected to be preferably in the range from 4 to 10 mm, even more preferably approximately 6 mm.

An echo-free, or at least, low-echo termination of the measuring device additionally can be improved, if so required, by providing an orifice at the second end of the semi-infinite tube. The diameter of the orifice is preferably selected in the range from 1.5 to 2 mm.

As already mentioned, it is advantageous to connect the toroidal space with a flushing gas supply. A permanent flushing gas supply is preferred. The flow of the flushing is preferably adjusted so that the flow velocity in the measuring tube is below 3 m/s.

The probe according to the invention is particularly suitable for use in gas turbines, wherein the measuring-point end of the measuring tube is open towards a combustor of the gas turbine. The toroidal space is preferably connected with the combustor plenum of the gas turbine. This ensures the flushing air supply as long as the gas turbine is operating, and the pressure of the flushing air is about 1 bar higher than the combustor pressure at the measuring-point end of the probe. This results in an inherently safe system, and the penetration of hot combustion gases into the probe, and thus any contact of hot gas with the pressure transmitter is reliably prevented. The flushing air is provided in this embodiment in a modern gas turbine at a temperature of about 350–400° C. or even higher. It is especially advantageous that the entire configuration is then designed so that the flushing air is cooled when flowing through the semi-infinite tube to a range of slightly above 100° C., for example, 120° C. to about 200° C. In a preferred embodiment, the flushing gas is at temperatures in the range from 150° C. to 180° C. by the time the flushing gas enters the measuring tube. This temperature range has the advantage that, on the one hand, condensation is prevented, but, on the other hand, a pressure transmitter, whose upper acceptable usage temperature is specified, for example, as 200° C., can be easily used. For this purpose, the winding carrier can be provided with ventilation openings. These openings ensure that atmospheric air is able to flow through the winding and around the semi-infinite tube, so that medium flowing within the semi-infinite tube is cooled.

When used in gas turbines, it is known that the pulsation values measured with the probe are used for regulating and protection actions. This means that when an acceptable upper value is exceeded, an emergency shutdown or protective relief of the machine can be initiated, or, adjustments of certain combustion parameters, such as the control of premix burners or water injection, can be made in relationship to measured combustor pulsations. Naturally, the probe according to the invention also can be used very well for other combustion chambers and hot gas flows.

BRIEF DESCRIPTION OF THE FIGURES

The invention is described in more detail below in reference to the drawings. In the drawings.

All figures should be understood as being solely instructional, and in no way restrict the scope of the invention as characterized in the claims.

DETAILED DESCRIPTION OF THE PREFERRED EMBODIMENTS

Figure 1:
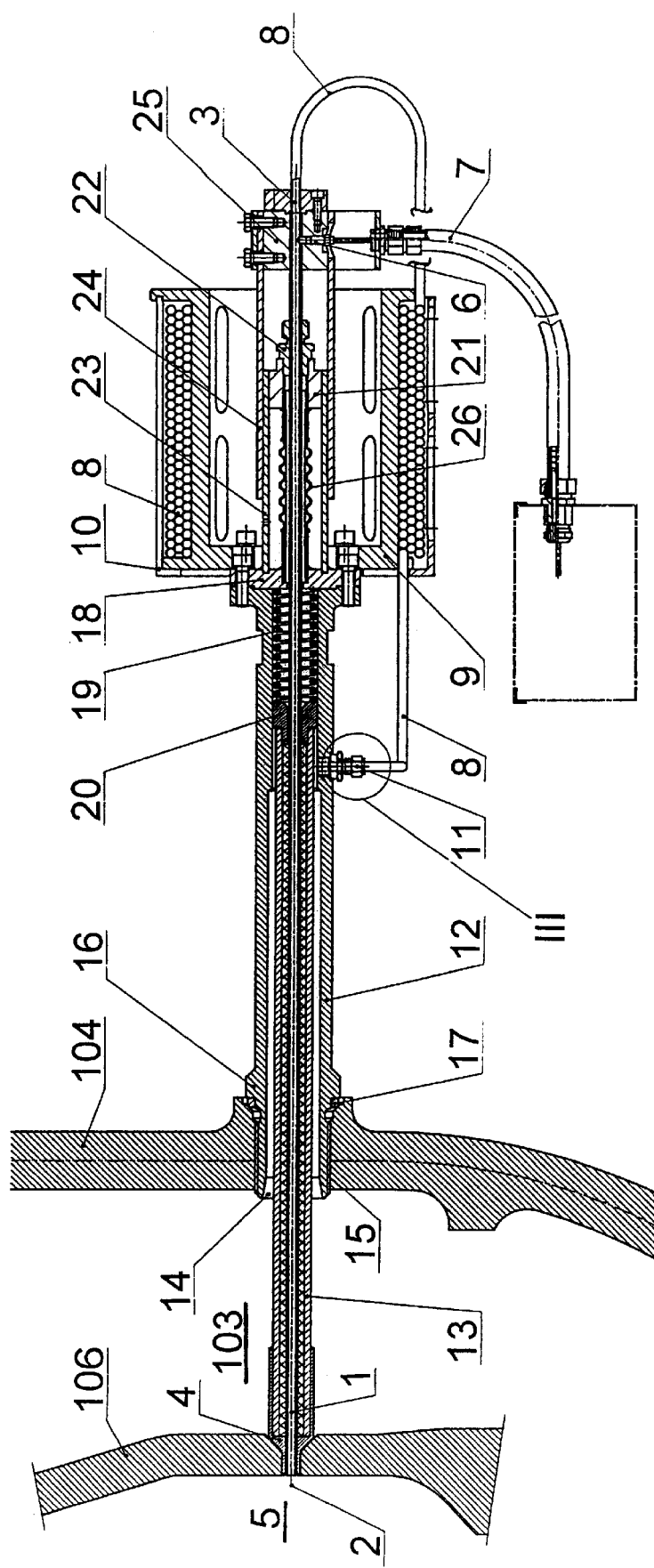
FIG. 1 shows a probe constructed according to an embodiment of the invention.

The probe illustrated in FIG. 1 comprises a measuring tube 1 with an end 2 at the measuring point side of the probe and an end 3 at the transmitter side of the probe. A cone seat 4 as illustrated may be used to achieve a gas-tight seal at the measuring point side of the probe. Other gas-tight types of the seat, e.g., a ball seat, familiar to the expert can be used. The opening of the measuring tube towards the combustor is constructed with a sharp edge and an abrupt and unsteady transition. This embodiment offers better acoustics than a rounded or conical transition. During the probe's installation, described in an exemplary manner in greater detail below with reference to FIG. 2, the seat 4 is pressed with a force against a tube branch of the measuring chamber 5, and in this way seals the seat 4 on the measuring point end of the measuring tube against the measuring point opening so as to be gas-tight. On the transmitter end 3 of the measuring tube 1, a pressure transmitter 6 is positioned, which measures the pressure in the measuring tube. The pressure transmitter preferably should be selected with the smallest possible dimensions, and is preferably positioned in such a manner on a radial, outer wall of the measuring tube that the smooth wall surface inside the measuring tube is interrupted as little as possible by steps. As a transmitter, for example, a piezoelectric transmitter or a sample microphone can be used. The pressure transmitter itself is preferably constructed with AC-coupling, i.e., does not emit a signal at a constant pressure. This has the advantage that measuring signals triggered by pressure fluctuations with amplitudes in the mbar range are not lost in the noise or high bias of the signal in the presence of absolute pressures of, for example, 30 bar.

According to an embodiment of the invention, a pressure present in a chamber 5, at which the measuring point end of the measuring tube terminates, is impressed on the inside of the measuring tube. This means that the pressure fluctuations in the measuring chamber 5 are also impressed on the measuring tube inside and are picked up by the pressure transmitter 6. Preferably pressure fluctuations with frequencies of several Hz to several kHz, roughly in the acoustic range, are converted into electric signals. The amplitude of the pressure fluctuations to be measured range from a magnitude of several $10^{-3}$ to several $10^{-2}$ of the absolute pressure, which emphasizes the advantage of a suppression of the bias of the pressure during the signal conversion. The electrical signal generated by the transmitter is passed on via a signal cable 7—whereby specially shielded cables are used—to data acquisition electronics, and is further processed there by means of different methods that are known per se. The function of this probe would be significantly hampered by any echoes resulting from the termination of the measuring tube. In order to prevent this, a semi-infinite tube is provided at the transmitter end of the measuring tube.

The semi-infinite tube is a seamlessly constructed line having a long length, preferably more than 40 m, for example 50 m, or even longer. The internal diameter of the tube is preferably identical as closely as possible with as little tolerance as possible, to the internal diameter of the measuring tube. The internal diameter of the measuring tube is preferably in the range from 4 to 8 mm, even more preferably approximately 6 mm. The dimensional precision in the manufacturing of the measuring tube and semi-infinite tube ensures a practically seamless transition from the measuring tube into the semi-infinite tube. This prevents the creation of reflection effects at the transition site. The semi-infinite tube is designated as semi-infinite because with the mentioned internal diameters, the pressure fluctuations to be measured—basically sound waves—are dissipated over this long length, and therefore can no longer be reflected at the end of the semi-infinite tube. This means that acoustically, the semi-infinite tube really acts in this direction as an infinite tube.

In practical use of the installation, the handling of the long tube was found to be extremely problematic in the long-line probes used up to now. Experience shows that components that are not very compact units are taken out of the way or stepped on, and that during continuous use a rather rough treatment must be expected. However, this is a very critical issue for a line designed as a semi-infinite tube. Such a line with an internal diameter of, for example, 6 mm, and an appropriate wall thickness is easily kinked or otherwise damaged at the inside wall, which consequently results in undesired reflections of pressure oscillations.

According to the invention, the probe is therefore provided with a winding carrier 9 that represents an integral component of the probe. The semi-infinite tube 8 is positioned as a winding on this winding carrier. This winding is additionally covered by a protective sleeve 10. This ensures the integrity of the semi-infinite tube even when assembly and maintenance staff step on the installed probe.

At a second end 11, the semi-infinite tube is connected to a flushing gas supply. The constructive design of the flushing gas supply poses very similar problems as the semi-infinite tube in practical use: In order to ensure its mechanical integrity, the flushing gas supply must not be installed "freely floating" but must be integrated into a compact unit. According to the invention, this is achieved by placing an outer tube 12 around the measuring tube. A toroidal space 14 is defined between the measuring tube 1 or an insulation material 13 enveloping the measuring tube and the outer pipe 12. Flushing gas can be introduced into this toroidal space. The flushing gas then flows through the semi-infinite tube and the measuring tube in the direction toward the measuring point end of the measuring tube. This prevents the penetration of hot and aggressive combustion gases into the measuring tube and the contact of the transmitter with the combustion gases. As a result, requirements on the temperature and corrosion resistance of the transmitter are more easily met. The permanent flow of the flushing gas furthermore ensures a substantially constant temperature inside the measuring tube over its length.

The winding carrier 9 fulfills another function in connection with the flushing gas supply. As already described above, it may easily occur in practical use that flushing gas is provided with a starting temperature of, for example, about 400° C. In this context, the winding carrier 9 is provided with openings that ensure free circulation of air around the windings of the semi-infinite tube 8. This air circulation is used specifically for cooling the flushing gas flowing inside the semi-infinite tube to a desired temperature of, for example, 150° C. to 200° C., more preferably approximately 180° C. In principle, it would also be conceivable to design the size of the ventilation openings so as to be adjustable in order to implement a regulation of the flushing gas temperature on entering the measuring tube in this manner.

Figure 2:
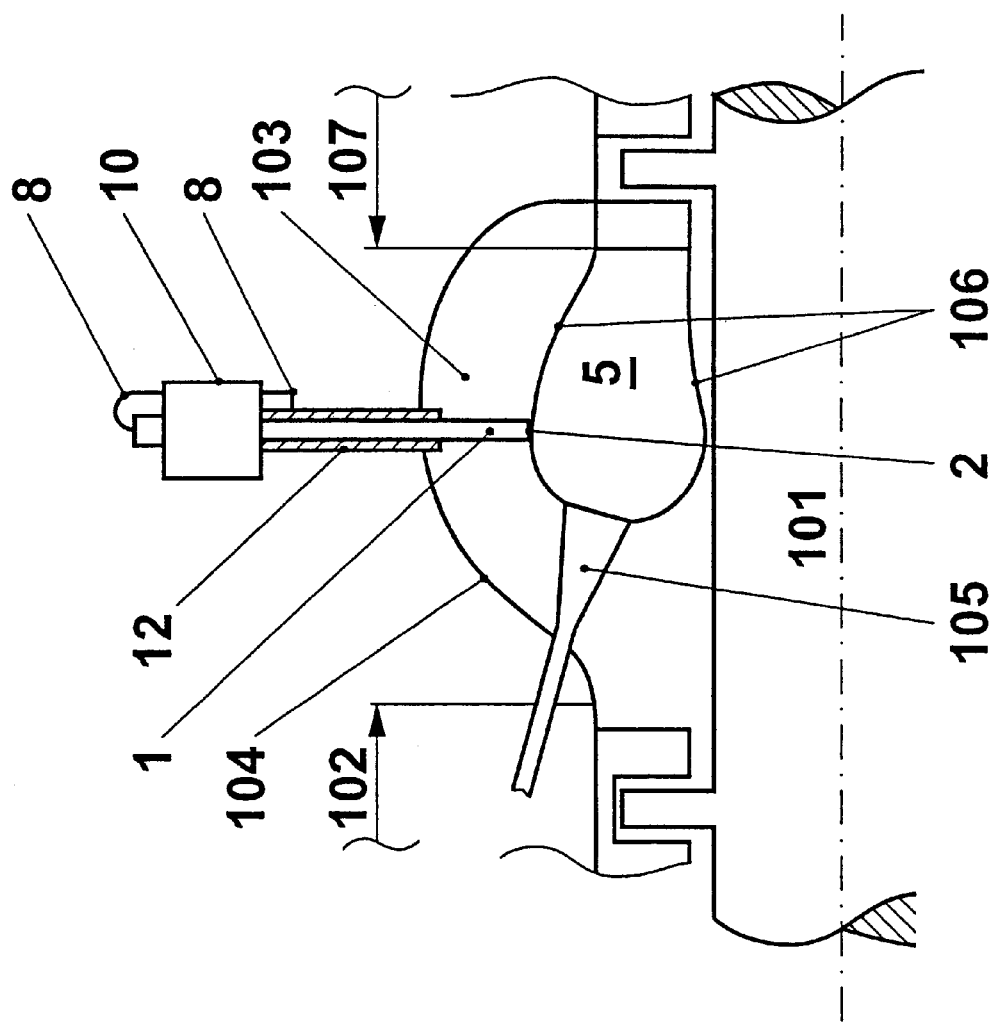
FIG. 2 shows an exemplary use of a probe according to an embodiment of the invention with a gas turbine.

Referring to FIG. 2, a longitudinal section of part of a gas turbine is illustrated. Only those details necessary for directly understanding the structure and function of the probe are shown. The man of ordinary skill in the art is perfectly familiar with the function of the rotor 101 and its rotating vanes. From a compressor section 102 of the gas turbine, compressed air flows into a combustor plenum 103 that is enclosed in an outer sleeve 104 of the gas turbine. The air flows through burner 105 into a combustor 5 of the gas turbine, said combustor being divided from the plenum by the burner hood 106. When flowing through the burner 105, the air typically undergoes a pressure drop in a magnitude of 0.5 to 1 bar. In the burner 105, the compressed air is mixed in a manner not shown here, and known per se, with an amount of fuel that is combusted in the combustor 5. The hot gas produced in this manner finally flows out of the combustor 5 through a turbine section 107, where the gases are expanded, producing mechanical power. Inhomogeneities occurring during the combustion result in pressure pulsations in the combustor, which under unfavorable conditions may reach critical amplitudes that also could threaten the mechanical integrity of the structures.

For this reason, the combustor of a gas turbine preferably should be provided with a measuring point that permits a continuous monitoring of the pressure pulsations. FIG. 2 shows the possible positioning of a probe according to the invention at a gas turbine for this purpose. For this purpose, an opening is provided in the hood 106. The measuring point end 2 of the measuring tube 1 of the probe is positioned at this opening. A through-opening in the outer sleeve 104 of the gas turbine is produced with a size suitable to also accept the outer tube 12. The toroidal space defined between the inner measuring tube and the outer tube is open towards the plenum. Because of the pressure drop across the burner(s), the pressure in the toroidal space is greater than that in the measuring tube, ensuring a flow of compressed air through the semi-infinite tube into the measuring tube. By connecting the flushing gas supply to the plenum, the flushing gas supply is inherently safe. As long as the gas turbine is operating, and combustion gases could potentially penetrate into the measuring tube and threaten the sensors, flushing gas that prevents this penetration of hot gas also will be present.

FIG. 1 illustrates the installation of the probe into a thermal machine, such as, for example, a gas turbine. The outer tube 12 is provided at a front end with an outer thread 15, with which it is screwed into the outer sleeve 104. The outer tube is screwed into the outer sleeve tightly and provided with a sealing ring or a sealing cord 17 in order to ensure a reliable sealing of the plenum pressure against external pressure. Naturally other devices known to the skilled person, for example, a flange joint, can be used for the attachment of the outer tube 12 to the outer sleeve 104 while achieving the desired sealing arrangement.

The measuring tube also forms a gas-tight termination at the hood 106 with a cone seat 4, and otherwise is passed through the hood 106 at the measuring point end 2, thereby forming a connection with the combustor 5. On a front side of the outer tube 12 facing away from the measuring point, a plate 18 is mounted. This plate 18 serves as a first support for a pressure spring 19. A second support 20 for the spring 19 is fixed to the measuring tube 1 and positioned in an axially movable manner in the outer tube 12. In this way, the pressure spring 19 is able to exert an axial force onto the measuring tube 1. The axial dimensions have been selected so that in the installed state an axial force is always exerted onto the measuring tube in such a way that a gas-tight seat of the cone seat 4 is ensured. In addition, the spring-loaded, axially movable positioning of the measuring tube in the outer tube ensures a compensation for differential expansions between the outer sleeve 104 and the hood 106 on the one hand, and between the measuring tube 1 and the outer tube 12 on the other hand. The tightness of the cone seat 4 on the hood 106 is thereby ensured.

The plate 18 is provided with an opening whose diameter is greater than that of the measuring tube. This prevents binding of the measuring tube in the outer tube. On the other hand, no gas-tight seat can be achieved between the axially movable support 20 and the outer tube, either. During operation, plenum pressure that still must be sealed off towards the atmosphere without hindering the axial movement between measuring tube and outer tube still exists at the through-opening of the plate 18. For this reason, the through-opening is followed in a gas-tight manner by a bellow 26 that is also attached to a bushing 21 in a gas-tight manner at a second end. This bushing is again provided with means 22 for a gas-tight tube connection, for example a swagelock connection, which provides a gas-tight seal with respect to the measuring tube. The bushing 21 is positioned axially movable with a close sliding fit in a sheath 23 and in this way also fixes the measuring tube radially. The sheath 23 is connected in a fixed manner via the plate 18 with the outer tube. A second sheath 24 also extends axially movable over sheath 23. This sheath radially supports the transmitter carrier 25 wherein, on the one hand, the transmitter 6 is held, and, on the other hand, the measuring tube is positioned in a fixed manner.

The robust, radial support of the measuring tube at 3 positioning points in the rear part, and the preload through the spring in the front part increase the natural vibration frequency of the actually thin and soft measuring tube. This prevents vibration damage during continuous operation over several $10^4$ operating hours. Additionally, vibrations of the entire measuring device, including the transmitter, that could potentially falsify the measurement are essentially prevented.

Figure 3:
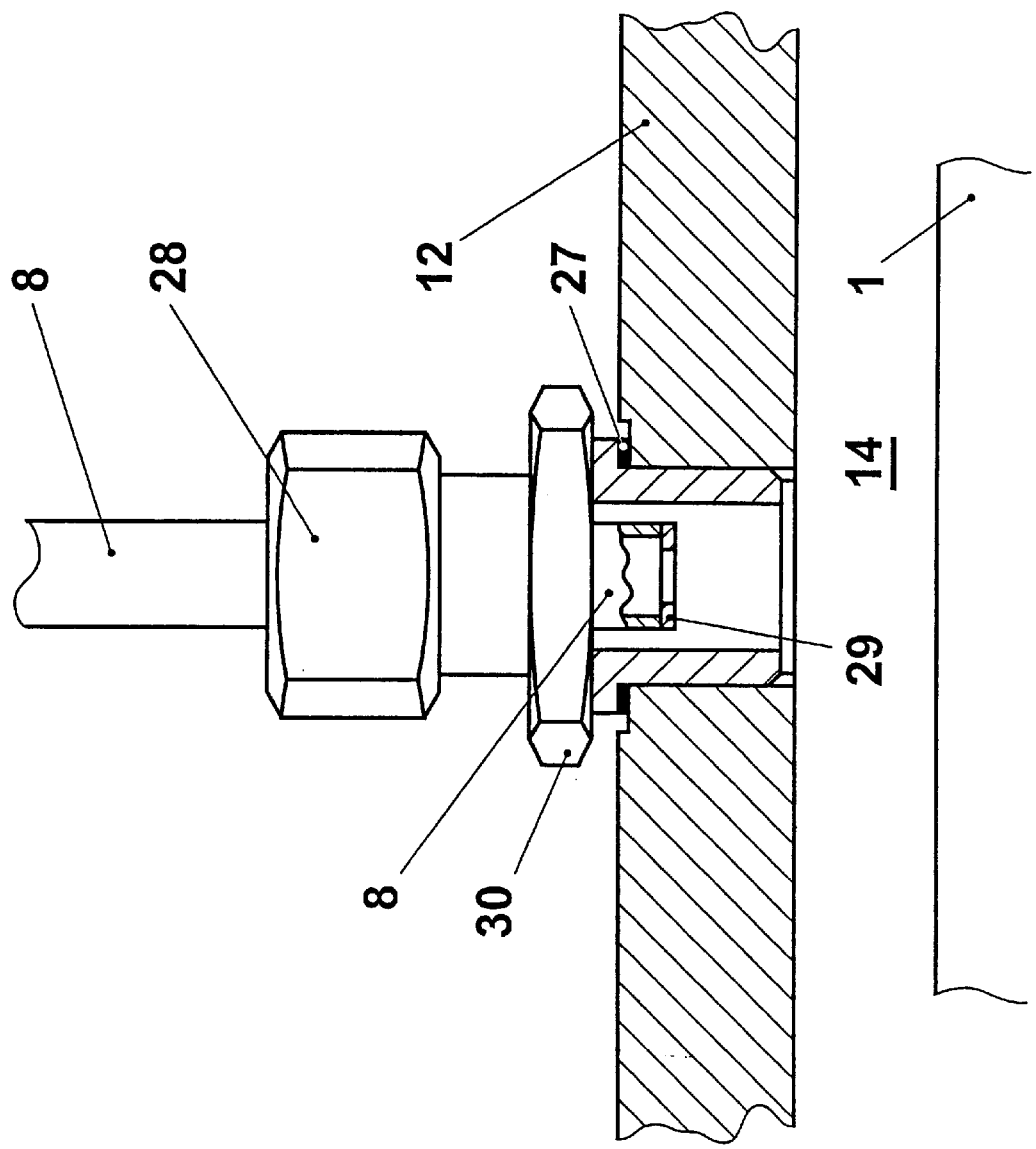
FIG. 3 shows a detailed illustration of an echo-free termination of the semi-infinite tube.

A probe according to the invention need not have all of the characteristics illustrated in the exemplary embodiment, or may be provided with other, different or additional structural characteristics or advantageous details, without deviating from the concept of the invention. Such a detail is shown in FIG. 3. Here, an enlarged detail shows the connection of the semi-infinite tube to the outer tube. A connecting branch 30 is screwed into the outer tube 12, whereby a sealing ring 27 is placed between the connecting branch and the outer tube. The tube 8 is passed through this connecting branch and is thus in fluid connection with the toroidal space 14. The nut 28 is positioned over the tube 8 and screwed onto the connecting branch 30 and in this manner produces a gas-tight connection at this point. The tube 8 is terminated by means of an orifice 29, which is, for example, welded on. Given a suitable design of the diameter of the orifice, the orifice also contributes to an echo-free termination of the semi-infinite tube. The internal diameter of the orifice is preferably selected in the range from 1.5 to 2 mm. The orifice also can be used for adjusting the flushing air flow.

Other embodiments and applications of the probe according to the invention will be obvious to the expert without deviating from the concept of the invention or exceeding the claimed scope of the invention.

What is claimed is:

1. A probe for measuring pressure oscillations, comprising:
    an inner measuring tube having a measuring point end and a transmitter end;
    an outer tube positioned to at least partially envelop the measuring tube, an outer wall of the measuring tube and an inner wall of the outer tube defining a toroidal space open to one side therebetween;
    a pressure transmitter connected with the interior of the measuring tube in the area of the transmitter end of the measuring tube; and
    a semi-infinite tube, a first end of the semi-infinite tube connected to the transmitter end of the measuring tube, and a second end of the semi-infinite tube connected to the toroidal space, the semi-infinite tube being constructed as a winding positioned around at least one of the measuring tube and the outer tube.

2. The probe according to claim 1, wherein the length of the semi-infinite tube is more than 7000 times the internal diameter of the semi-infinite tube.

3. The probe according to claim 1, wherein the semi-infinite tube has a length of more than 40 meters.

4. The probe according to claim 1, wherein the semi-infinite tube has substantially the same internal diameter as the measuring tube.

5. The probe according to claim 1, wherein the internal diameter of the measuring tube is in the range from 4 to 10 mm.

6. The probe according to claim 1, wherein the internal diameter of the measuring tube is 6 mm.

7. The probe according to claim 1, wherein an orifice is positioned at a transition from the semi-infinite tube to the toroidal space.

8. The probe according to claim 1, wherein the toroidal space is connected to a flushing gas supply.

9. The probe according to claim 8, wherein the temperature of the flushing gas entering the measuring tube at the transmitter end of the measuring tube is in the range from 120° C. to 200° C.

10. The probe according to claim 8, wherein the temperature of the flushing gas entering the measuring tube at the transmitter end of the measuring tube is in the range from 150° C. to 180° C.

11. A method of using a probe according to any one of claims 1–10, wherein:
    the measuring point end of the measuring tube is open towards a combustor of the gas turbine.

12. A method of using a probe according to any one of claims 1–10, wherein:
    the measuring point end of the measuring tube is open towards a combustor of the gas turbine, and the toroidal space is connected to a plenum of the gas turbine.

* * * * *